(12) United States Patent
Schmidt et al.

(10) Patent No.: US 6,667,291 B2
(45) Date of Patent: Dec. 23, 2003

(54) METHOD OF DETECTING AND TREATING CANCER

(75) Inventors: Carl J Schmidt, Exton, PA (US); Xin-Min Wang, Schwenksville, PA (US)

(73) Assignee: SmithKline Beecham Corporation, Philadelphia, PA (US)

(*) Notice: Subject to any disclaimer, the term of this patent is extended or adjusted under 35 U.S.C. 154(b) by 2 days.

(21) Appl. No.: 09/423,186

(22) PCT Filed: Jun. 9, 1998

(86) PCT No.: PCT/US98/12053

§ 371 (c)(1),
(2), (4) Date: Nov. 3, 1999

(87) PCT Pub. No.: WO98/56248

PCT Pub. Date: Dec. 17, 1998

(65) Prior Publication Data

US 2003/0175279 A1 Sep. 18, 2003

Related U.S. Application Data

(60) Provisional application No. 60/049,015, filed on Jun. 9, 1997.

(51) Int. Cl.$^7$ ................................................. A61K 38/00
(52) U.S. Cl. ............................... 514/2; 436/86; 436/105
(58) Field of Search ................................ 514/2; 436/86, 436/105

(56) References Cited

U.S. PATENT DOCUMENTS 5,696,092 A   12/1997   Patierno et al. ................ 514/21

FOREIGN PATENT DOCUMENTS

| WO | WO 96/38463 | 12/1996 |
| WO | WO 97/34997 | 9/1997 |
| WO | WO 98/07857 | 2/1998 |
| WO | WO 98/21331 | 5/1998 |

OTHER PUBLICATIONS

Becker et al., "Identification of Mammaglobin B, a Novel Member of the Uteroglobin Gene Family", Genomics 1998 54:70–78.

Chilton et al., "Zinc Finger Proteins RUSH in Where Others-Fear to Tread", Biol. of Reprod. 1998 58:285–294.

Lehrer et al., "Lipophilin, a novel Heterodimeric protein of human tears", FEBS Letters 1998 432:163–167.

Scholz et al., "Hormone–induced Recruitment of Spl Mediates Estrogen Activation of Rabbit Uterglobin Gene in Endometrial Epithelium", JBC 1998 273 (8):4360–4366.

Shibata et al., "Altered expression of transforming growth factor βs during urethral and bulbourethral gland tumor progression in transgenic mice carrying the androgen–responsive C3 (1) 5' flanking region fused to SV40 large T antigen", Carcinogenesis 1998 19 (1):195–205.

Watson et al., "Structure and transcriptional regulation of the human mammaglobin gene, a breast cancer associated member of the uteroglobin gene family localized to Chromosome 11q13", Oncogene 1998 16:817–824.

Yoshidome et al., Genetic alterations in the development of mammary and prostate cancer in the C3(1)/Tag transgenic mouse model (Review). Int. J. Oncology 1998 12:449–453.

Database Genebank, Accession No. AAC79996, Becker et al., Mammaglobin B precursor [Homo sapiens], 1998 see sequence.

Watson et al., Mammaglobin, a Mammary–specific Member of the Uteroglobin Gene Family, Is Overexpressed in Human Breast Cancer[1], Cancer Research 1996 56:380–865.

*Primary Examiner*—Zohreh Fay
(74) *Attorney, Agent, or Firm*—Licata & Tyrrell P.C.

(57) ABSTRACT

The present invention relates, in part, to newly developed assay for diagnosing cancers, particularly endometrial and mammary, endometriosis and endometrial fibroids along with methods for identifying therapeutic agents that modulate endometrial steroid binding protein II activity for the treatment of the above disorders.

8 Claims, No Drawings

METHOD OF DETECTING AND TREATING CANCER

This application is a 371 of PCT/US98/12053, filed on Jun. 9, 1998, which claims priority of appln 60/049,015 filed Jun. 9, 1999.

FIELD OF THE INVENTION

This invention relates, in part, to newly developed assay for diagnosing cancers, particularly endometrial and mammary, endometriosis and endometrial fibroids along with methods for identifying therapeutic agents that modulate Endometrial steroid binding protein II activity for treatment of the above disorders.

BACKGROUND OF THE INVENTION

Endometrial cancer occurs at a rate of approximately 44,500 new cases per year with approximately 10,000 deaths per year. If diagnosed and treated early, when the cancer is still confined to the endometrium, cure can be achieved in approximately 95% of the cases by hysterectomy. Pap smears can show endometrial cancers but are effective in only 50% of the cases. For the remainder, abnormal vaginal bleeding is typically the first clinical sign of endometrial cancer. There is a great need for sensitive methods for the detection of organ-confined endometrial cancer.

Steroid binding proteins, including uteroglobin and CC10, are a class of proteins which bind steroids along with methylsulfonyl metabolites of polychlorinated biphenyls. The exact function of members of this class of protein is uncertain, but uteroglobin has been shown to inhibit $PLA_2$ mediated responses. The gene and gene product of the present invention display homology to uteroglobin and CC10, show elevated expression of mRNA in endometrial cancer samples and is expressed in mammary tissue. This gene encoded product will be referred to as Endometrial Steroid Binding Protein II (ESBPII), and their polypeptide and polynucleotide sequences are given in Table 1 and 2, respectively.

SUMMARY OF THE INVENTION

Toward these ends, and others, it is an object of the present invention to provide a new method for diagnosing, treating, and monitoring progression, remission or recurrence of various forms of abnormal cell growth, such as cancers, particulary endometrial and mammary cancer, and endometriosis and endometrial fibroids. Further provided are methods to screen for therapeutic agents and pharmaceutical compositions for treating abnormal cell growth, such as cancers, particular endometrial and mammary cancer, and endometriosis and endometrial fibroids. Further provided is the utilization of such agents or compositions for the treatement abnormal cell growth, particulary endometrial and mammary cancer and endometriosis and endometrial fibroids.

Thus, in accordance with one aspect of the present invention there are provided methods of screening for compounds which bind to and inhibit activation of the ESBPII.

In accordance with another aspect of the present invention there is provided a method of using such inhibiting compounds for treating conditions associated with over-expression of the ESBPII.

In accordance with yet another aspect of the present invention, there are provided ESBPII antagonists (inhibitors). Among the preferred antagonists are those which mimic ESBPII so as to bind to ESBPII binding molecules but not elicit a ESBPII-induced response or more than one ESBPII-induced response. Also among the preferred antagonists are molecules that bind to or interact with ESBPII so as to inhibit an effect of ESBPII or more than one effect of ESBPII or which prevent expression of ESBPII.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

DESCRIPTION OF THE INVENTION

The present invention relates to diagnostic assays, both quantitative and qualitative for detecting levels of ESBPII protein or ESBPII mRNA in cells, tissues and bodily fluids, including determination of normal and abnormal levels. Thus, for instance, a diagnostic assay in accordance with the invention for detecting over-expression of ESBPII protein compared to normal control bodily fluids or tissue samples may be used to detect the presence of cancers, including endometrial and mammary cancer. Assay techniques that can be used to determine levels of gene expression, such as ESBPII of the present invention, in a sample derived from a host are well-known to those of skill in the art. Such assay methods include radioimmunoassays, reverse transcriptase PCR (RT-PCR) assays, gridding, immunohistochemistry assays, in situ hybridization assays, competitive-binding assays, Western Blot analyses and ELISA assays. Among these, ELISAs are frequently preferred to detect a gene's expressed protein in biological fluids. An ELISA assay initially comprises preparing an antibody, if not readily available from a commercial source, specific to ESBPII, preferably a monoclonal antibody. In addition a reporter antibody generally is prepared which binds specifically to ESBPII. The reporter antibody is attached to a detectable reagent such as radioactive, fluorescent or enzymatic reagent, for example horseradish peroxidase enzyme or alkaline phosphatase.

To carry out the ELISA, antibody specific to ESBPII is incubated on a solid support, e.g. a polystyrene dish, that binds the antibody. Any free protein binding sites on the dish are then covered by incubating with a non-specific protein such as bovine serum albumin. Next, the sample to be analyzed is incubated in the dish, during which time ESBPII binds to the specific antibody attached to the polystyrene dish. Unbound sample is washed out with buffer. A reporter antibody specifically directed to ESBPII and linked to horseradish peroxidase is placed in the dish resulting in binding of the reporter antibody to any monoclonal antibody bound to ESBPII. Unattached reporter antibody is then washed out. Reagents for peroxidase activity, including a colorimetric substrate are then added to the dish. Immobilized peroxidase, linked to ESBPII antibodies, produces a colored reaction product. The amount of color developed in a given time period is proportional to the amount of ESBPII protein present in the sample. Quantitative results typically are obtained by reference to a standard curve. Without limiting the instant invention, typically, for a quantitative diagnostic assay a positive result indicating the disease is one in which blood levels are higher than three standard deviations above the mean blood level for a normal healthy population of individuals (99.86% of the population).

A competition assay may be employed wherein antibodies specific to ESBPII attached to a solid support and labeled ESBPII and a sample derived from the host are passed over the solid support and the amount of label detected attached to the solid support can be correlated to a quantity of ESBPII in the sample.

Nucleic acid methods may be used to detect ESBPII mRNA as a marker for abnormal cell growth including endometrial cancer, mammary cancer, endometriosis and endometrial fibroids. Polymerase chain reaction (PCR) and other nucleic acid methods, such as ligase chain reaction (LCR) and nucleic acid sequence based amplification (NASABA), can be used to detect malignant cells for diagnosis and monitoring of various malignancies. For example, reverse-transcriptase PCR (RT-PCR) is a powerful technique which can be used to detect the presence of a specific mRNA population in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction. RT-PCR can thus reveal by amplification the presence of a single species of mRNA. Accordingly, if the mRNA is highly specific for the cell that produces it, RT-PCR can be used to identify the presence of a specific type of cell.

Hybridization to clones arrayed on a grid can be used to both detect the expression of and quantitate the level of expression of that gene (gridding). In this approach, a cDNA encoding the ESBP II gene is fixed to a substrate. The substrate may be of any suitable type including but not limited to glass, nitrocellulose, nylon or plastic. DNA encoding the ESBP II clone is attached to the substrate and then incubated with the analyte, which may be RNA or a complementray DNA (cDNA) copy of the RNA, isolated from the tissue of interest. Hybridization between the substrate bound clone and the analyte can be detected and quantitated by several means including but not limited to radioactive labeling or fluorescence labeling of the analyte or a secondary molecule designed to detect the hybrid. Quantitation of the level of gene expression can be done by comparison of the intensity of the signal from the analyte compared with that determined from known standards. The standards can be obtained by in vitro transcription of the target gene, quantitating the yield, and then using that material to generate a standard curve.

The above tests can be carried out on samples derived from patients' bodily fluids and tissue extracts (homogenates or solubilized tissue) such as from blood, urine, saliva, tissue biopsy and autopsy material.

Antibodies

The ESBPII polypetide, its fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of a Fab expression library. Various procedures known in the art may be used for the production of such antibodies and fragments.

Antibodies generated against ESBPII can be obtained by direct injection of the polypeptide into an animal or by administering the polypeptide to an animal, preferably a nonhuman. The antibody so obtained will then bind the polypeptide itself. In this manner, even a sequence encoding only a fragment of the polypeptide can be used to generate antibodies binding the whole native polypeptide.

For preparation of monoclonal antibodies, any technique which provides antibodies produced by continuous cell line cultures can be used. Examples include the hybridoma technique (Kohler, G. and Milstein, C., Nature 256:495–497 (1975)), the trioma technique, the human B-cell hybridoma technique (Kozbor et al., Immunology Today 4:72 (1983)) and the EBV-hybridoma technique to produce human monoclonal antibodies (Cole et al., pg. 77–96 in MONOCLONAL ANTIBODIES AND CANCER THERAPY, Alan R. Liss, Inc. (1985)).

Techniques described for the production of single chain antibodies (U.S. Pat. No. 4,946,778) can be adapted to produce single chain antibodies to immunogenic polypeptide products of this invention. Also, transgenic mice, or other organisms such as other mammals, may be used to express humanized antibodies to immunogenic ESBPII.

Thus, among others, antibodies against ESBPII may be employed to treat/inhibit various forms of abnormal cell growth, including endometrial and mammary cancer, along with endometriosis and endometrial fibroids.

ESBPII Binding Molecules and Assays

ESBPII could be used to isolate proteins which interact with it and this interaction could be a target for interference. Inhibitors of protein-protein interactions between ESBPII and other factors could lead to the development of pharmaceutical agents for the modulation of ESBPII activity. As used herein, the term "modulate" refer to affecting the ESBPII function.

Thus, this invention also provides a method for identification of binding molecules to ESBPII. Genes encoding proteins for binding molecules to ESBPII can be identified by numerous methods known to those of skill in the art, for example, ligand panning and FACS sorting. Such methods are described in many laboratory manuals such as, for instance, Coligan et al., Current Protocols in Immunology I (Rivett, A. J. Biochem. J. 291:1–10 (1993)): Chapter 5 (1991).

For example, the yeast two-hybrid system provides methods for detecting the interaction between a first test protein and a second test protein, in vivo, using reconstitution of the activity of a transcriptional activator. The method is disclosed in U.S. Pat. No. 5,283,173; reagents are available from Clontech and Stratagene. Briefly, ESBPII cDNA is fused to a Gal4 transcription factor DNA binding domain and expressed in yeast cells. cDNA library members obtained from cells of interest are fused to a transactivation domain of Gal4. cDNA clones which express proteins which can interact with ESBPII will lead to reconstitution of Gal4 activity and transactivation of expression of a reporter gene such as Gal1-lacZ.

An alternative method is screening of λgt11, λZAP (Stratagene) or equivalent cDNA expression libraries with recombinant ESBPII. Recombinant ESBPII protein or fragments thereof are fused to small peptide tags such as FLAG, HSV or GST. The peptide tags can possess convenient phosphorylation sites for a kinase such as heart muscle creatine kinase or they can be biotinylated. Recombinant ESBPII can be phosphorylated with $^{32}$[P] or used unlabeled and detected with streptavidin or antibodies against the tags. λgt11cDNA expression libraries are made from cells of interest and are incubated with the recombinant ESBPII, washed and cDNA clones isolated which interact with ESBPII. See, e.g., T. Maniatis et al, supra.

Another method is the screening of a mammalian expression library in which the cDNAs are cloned into a vector between a mammalian promoter and polyadenylation site and transiently transfected in COS or 293 cells followed by detection of the binding protein 48 hours later by incubation of fixed and washed cells with a labelled ESBPII, preferably iodinated, and detection of bound ESBPII by autoradiography. See Sims et al., *Science* 241:585–589 (1988) and McMahan et al., *EMBO J.* 10:2821–2832 (1991). In this manner, pools of cDNAs containing the cDNA encoding the binding protein of interest can be selected and the cDNA of interest can be isolated by further subdivision of each pool followed by cycles of transient transfection, binding and autoradiography. Alternatively, the cDNA of interest can be isolated by transfecting the entire cDNA library into mammalian cells and panning the cells on a dish containing ESBPII bound to the plate. Cells which attach after washing are lysed and the plasmid DNA isolated, amplified in bacteria, and the cycle of transfection and panning repeated until a single cDNA clone is obtained. See Seed et al, *Proc. Natl. Acad. Sci. USA* 84:3365 (1987) and Aruffo et al., *EMBO J.* 6:3313 (1987). If the binding protein is secreted, its cDNA can be obtained by a similar pooling strategy once a binding or neutralizing assay has been established for assaying supernatants from transiently transfected cells. General methods for screening supernatants are disclosed in Wong et al., *Science* 228:810–815 (1985).

Another alternative method is isolation of proteins interacting with ESBPII directly from cells. Fusion proteins of ESBPII with GST or small peptide tags are made and immobilized on beads. Biosynthetically labeled or unlabeled protein extracts from the cells of interest are prepared, incubated with the beads and washed with buffer. Proteins interacting with ESBPII are eluted specifically from the beads and analyzed by SDS-PAGE. Binding partner primary amino acid sequence data are obtained by microsequencing. Optionally, the cells can be treated with agents that induce a functional response such as tyrosine phosphorylation of cellular proteins. An example of such an agent would be a growth factor or cytokine such as interleukin-2.

Another alternative method is immunoaffinity purification. Recombinant ESBPII is incubated with labeled or unlabeled cell extracts and immunoprecipitated with anti-ESBPII antibodies. The immunoprecipitate is recovered with protein A-Sepharose and analyzed by SDS-PAGE. Unlabelled proteins are labeled by biotinylation and detected on SDS gels with streptavidin. Binding partner proteins are analyzed by microsequencing. Further, standard biochemical purification steps known to those skilled in the art may be used prior to microsequencing.

Yet another alternative method is screening of peptide libraries for binding partners. Recombinant tagged or labeled ESBPII is used to select peptides from a peptide or phosphopeptide library which interact with ESBPH. Sequencing of the peptides leads to identification of consensus peptide sequences which might be found in interacting proteins.

ESBPII binding partners identified by any of these methods or other methods which would be known to those of ordinary skill in the art as well as those putative binding partners discussed above can be used in the assay method of the invention. Assaying for the presence of ESBPII/binding partner complex are accomplished by, for example, the yeast two-hybrid system, ELISA or immunoassays using antibodies specific for the complex. In the presence of test substances which interrupt or inhibit formation of ESBPII/binding partner interaction, a decreased amount of complex will be determined relative to a control lacking the test substance.

Assays for free ESBPII or binding partner are accomplished by, for example, ELISA or immunoassay using specific antibodies or by incubation of radiolabeled ESBPII with cells or cell membranes followed by centrifugation or filter separation steps. In the presence of test substances which interrupt or inhibit formation of ESBPII/binding partner interaction, an increased amount of free ESBPII or free binding partner will be determined relative to a control lacking the test substance.

Polypeptides of the invention also can be used to assess ESBPII binding capacity of ESBPII binding molecules in cells or in cell-free preparations.

Agonists and Antagonists—Assays and Molecules

The ESBPII may be employed in a process for screening for compounds which either inhibit, promote or modulate the activity of ESBPII.

Examples of potential ESBPII antagonists are small molecules such as organic molecules or peptides, antibodies, or in some cases an oligonucleotide, which binds to ESBPII and prevents activity.

Potential antagonists also include small molecules or proteins which are closely related to the binding molecules of the ESBPII, e.g. a fragment of the binding molecules, which have lost biological function, and when bind to the ESBPII polypeptide inhibit its activity. "Binding molecules" as used herein refer to molecules that specifcally bind to or interact with ESBPII polypeptide of the present invention. Included in the definition of binding molecules are other factors, co-factors, units or subunits which enhance ESBPII activity or diminish it. Such binding molecules are a part of the present invention. Binding molecules also may be non-naturally occurring, such as antibodies and antibody-derived reagents that bind specifically to ESBPII.

A potential antagonist also includes an antisense construct prepared through the use of antisense technology. Antisense technology can be used to control gene expression through triple-helix.formation or antisense DNA or RNA, both of which methods are based on binding of a polynucleotide to DNA or RNA. For example, the 5' coding portion of the polynucleotide sequence, which encodes for the mature ESBPII, is used to design an antisense RNA oligonucleotide of from about 10 to 40 base pairs in length. A DNA oligonucleotide is designed to be complementary to a region of the gene involved in transcription (triple helix -see Lee et al., *Nucl. Acids Res.,* 6:3073 (1979); Cooney et al., *Science,* 241:456 (1988); and Dervan et al., *Science,* 251:1360 (1991)), thereby preventing transcription and the production of ESBPII polypeptide. The antisense RNA oligonucleotide hybridizes to the mRNA in vivo and blocks translation of the mRNA molecule into the ESBPII polypeptide (antisense—Okano, *J. Neurochem.,* 56:560 (1991); Oligodeoxynucleotides as Antisense Inhibitors of Gene Expression, CRC Press, Boca Raton, Fla. (1988)). The oligonucleotides described above can also be delivered to cells such that -the antisense RNA or DNA may be expressed in vivo to inhibit production of the ESBPII polypeptide. Included in this delivery is by gene therapy.

Another potential antagonist is a small molecule which binds to the ESBPII making it inaccessible to binding molecules (e.g. substrates) such that normal biological activity is prevented. Examples of small molecules include, but are not limited to, small peptides or peptide-like molecules and organic compounds.

This invention additionally provides a method of treating an abnormal condition related to an excess of ESBPII activity, such as endometrial and mammary cancer, endometriosis and endometrial fibroids, which comprises administering to a subject the inhibitor compounds (antagonists) as hereinabove described along with a pharmaceutically acceptable carrier in an amount effective to inhibit ESBPII activity directly or by blocking binding of binding molecules to ESBPII polypeptide.

Compositions and Kits

The compounds which inhibit such ESBPII, may be employed in combination with a suitable pharmaceutical carrier. Such compositions comprise a therapeutically effective amount of the polypeptide or compound, and a pharmaceutically acceptable carrier or excipient. Such a carrier includes but is not limited to saline, buffered saline, dextrose, water, glycerol, ethanol, and combinations thereof. The formulation should suit the mode of administration.

The invention further relates to pharmaceutical packs and kits comprising one or more containers filled with one or more of the ingredients of the aforementioned compositions of the invention.

Administration

Polypeptides and other compounds of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes, among others.

The pharmaceutical compositions generally are administered in an amount effective for treatment or prophylaxis of a specific indication or indications. In general, the compositions are administered in an amount of at least about 10 µg/kg body weight. In most cases they will be administered in an amount not in excess of about 8 mg/kg body weight per day. Preferably, in most cases, dose is from about 10 µg/kg to about 1 mg/kg body weight, daily. It will be appreciated that optimum dosage will be determined by standard methods for each treatment modality and indication, taking into account the indication, its severity, route of administration, complicating conditions and the like.

Vaccine

Another aspect of the invention relates to a method for inducing an immunological response in an animal, particularly in a mammal, which comprises inoculating the animal with ESBPII, or a fragment or variant thereof, adequate to produce antibody to protect said animal from diseases of abnormal cell growth such as as endometrial and mammary cancer, endometriosis and endometrial fibroids. Yet another aspect of the invention relates to a method of inducing immunological response in an animal which comprises, through gene therapy, delivering gene encoding ESBPII, or a fragment or a variant thereof, for expressing ESBPII, or a fragment or a variant thereof in vivo in order to induce an immunological response to produce antibody to protect said animal from disease.

Further aspect of the invention relates to an immunological composition which, when introduced into an animal, particularly mammalian host, induces an immunological response in that animal to a given ESBPII gene or protein coded therefrom, wherein the composition comprises a recombinant ESBPHI gene or protein coded therefrom comprising DNA which codes for and expresses an antigen of said ESBPII gene or protein coded therefrom.

The ESBPII or a fragment thereof may be fused with co-protein which may not by itself produce antibodies, but is capable of stabilizing the first protein and producing a fused protein which will have immunogenic and protective properties. Thus fused recombinant protein, preferably further comprises an antigenic co-protein, such as Glutathione-S-transferase (GST) or beta-galactosidase, relatively large co-proteins which solubilize the protein and facilitate production and purification thereof. Moreover, the co-protein may act as an adjuvant in the sense of providing a generalized stimulation of the immune system. The co-protein may be attached to either the amino or carboxy terminus of the first protein.

The present invention also includes a vaccine formulation which comprises the immunogenic recombinant protein together with a suitable carrier. Since the protein may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain antioxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Whilst the invention has been described with reference to ESBPII, it is to be understood that this covers fragments of the naturally occurring protein and similar proteins (for example, having sequence homologies of 50% or greater) with additions, deletions or substitutions which do not substantially affect the immunogenic properties of the recombinant protein.

The present invention also provides a method for the production of transgenic animals with altered ESBPII levels for the productions of animals bearing ESBPII induced diseases. Transgenic, non-human, animals may be obtained by transfecting appropriate fertilized eggs or embryos of a host with nucleic acids encoding the ESBPII disclosed herein, see for example U.S. Pat. Nos. 4,736,866; 5,175,385; 5,175,384 and 5,175,386. The resultant transgenic animal may be used as a model for the study of altered ESBPII levels. Particularly, useful transgenic animals are those which display a detectable phenotype associated with the altered expression of the ESBPII polypeptide. Drugs may then be screened for their ability to reverse or exacerbate the relevant phenotype.

TABLE I[a]

```
         10                  30                  50
          .                   .                   .
MKLSVCLLLVTLALCCYQANAEFCPALVSELLDFFFISEPLFKLSLAKFDAPPEAVAAKL 70                  90
          .                   .
GVKRCTDQMSLQKRSLIAEVLVKILKKCSV
```

[a]Endometrial Steroid Binding Protein II (SEQ ID NO: 1)

TABLE II[b]

```
         10                  30                  50
TTGTTTGTGAAAGCTGAGCTCACAGCAAAACAAGCCACCATGAAGCTGTCGGTGTGTCTC 70                  90                 110
CTGCTGGTCACGCTGGCCCTCTGCTGCTACCAGGCCAATGCCGAGTTCTGCCCAGCTCTT 130                 150                 170
GTTTCTGAGCTGTTAGACTTCTTCTTCATTAGTGAACCTCTGTTCAAGTTAAGTCTTGCC 190                 210                 230
AAATTTGATGCCCCTCCGGAAGCTGTTGCAGCCAAGTTAGGAGTGAAGAGATGCACGGAT 250                 270                 290
CAGATGTCCCTTCAGAAACGAAGCCTCATTGCGGAAGTCCTGGTGAAAATATTGAAGAAA 310                 330                 350
TGTAGTGTGTGACATGTAAAAACTTCATCCTGGTTTCCACTGTCTTTCAATGACACCCTG 370                 390                 410
ATCTTCACTGCAGAATGTAAAGGTTTCAACGTCTTGCTTTAATAAATCACTTGCTCTCCAA

AAAAAAAAAAA
```

[b]Endometrial steroid binding protein II nucleotide sequence (SEQ ID NO: 2)

EXAMPLES

The present invention is further described by the following examples. The examples are provided solely to illustrate the invention by reference to specific embodiments. These exemplification's, while illustrating certain specific aspects of the invention, do not portray the limitations or circumscribe the scope of the disclosed invention.

All examples are carried out using standard techniques, which are well known and routine to those of skill in the art, except where otherwise described in detail. Routine molecular biology techniques of the following examples can be carried out as described in standard laboratory manuals, such as Sambrook et al., MOLECULAR CLONING: A LABORATORY MANUAL, 2nd Ed.; Cold Spring Harbor Laboratory Press, Cold Spring Harbor, N.Y. (1989), herein referred to as "Sambrook."

All parts or amounts set out in the following examples are by weight, unless otherwise specified.

Unless otherwise stated size separation of fragments in the examples below is carried out using standard techniques of agarose and polyacrylamide gel electrophoresis ("PAGE") in Sambrook and numerous other references such as, for instance, by Goeddel et al., *Nucleic Acids Res.* 8:4057 (1980).

Example 1

To evaulate the level of ESBPII in normal and endometrial tumor tissue, mRNA was extracted from two endometrial tumors and matched normal tissues. Subsequently, first strand cDNA was prepared with reverse transcriptase and the polymerase chain reaction was done using primers specific to ESBPII. Results were normalized by using the same amount of starting cDNA in each sample. When the resulting products were analyzed by gel electrophoresis followed by ethdium bromide detection, ESBPII was found to be expressed in the endometrial tumors at least 5 fold greater in the endometrial tumor tissue relative to the normal adjacent tissue.

Example 2

To determine the tissue distribution of ESBPII expression, mRNA and cDNA was prepared from a variety of tissues and the polymerase chain reaction was done using the ESBPII primers. Results are indicated below:

| | |
|---|---|
| Endometrium | + |
| Endometrial Cancer | +++++ |
| Mammary | ++ |
| Prostate | Absent |
| Colon | Absent |
| Colon Cancer | Absent |
| Lung | Absent |
| Lung Cancer | Absent |
| Liver | Absent |
| Liver Cancer | Absent |
| Pancreas | Absent |
| Heart | Absent |
| Skeletal Muscle | Absent |
| Peripheral Blood Cells | Absent |

What is claimed is:

1. A diagnostic method for endometrial cancer, mammary cancer, endometriosis or endometrial fibroids comprising:

analyzing for the abnormally high level of ESBPII polypeptide in cells, tissues and bodily fluids.

2. A method of claim 1 in which the diagnostic process involves ELISA.

3. A method of claim 1 in which the diagnostic process is immunohistochemistry.

4. A diagnostic method for mammary cancer, endometrial cancer, endometriosis or endometrial fibroids comprising:

analyzing for the abnormally high or low transcription level of ESBPII in cells, tissues and bodily fluids.

5. A method of claim 4 in which the diagnostic process involves Northern blot analysis.

6. A method of claim 4 in which the diagnostic process involves in situ hybridization.

7. A method of claim 4 in which the diagnostic process involves RT-PCR.

8. A method of claim 4 in which the diagnostic process involves gridding.

* * * * *